United States Patent [19]

Chen et al.

[11] Patent Number: 5,807,570
[45] Date of Patent: Sep. 15, 1998

[54] TRANSDERMAL ADMINISTRATION OF ROPINIROLE AND ANALOGS THEREOF

[75] Inventors: Tung-Fen Chen, Sunnyvale; Chia-Ming Chiang, Foster City, both of Calif.

[73] Assignee: Cygnus, Inc., Redwood City, Calif.

[21] Appl. No.: 708,409

[22] Filed: Sep. 4, 1996

Related U.S. Application Data

[63] Continuation-in-part of Ser. No. 537,325, Sep. 29, 1995, abandoned.

[51] Int. Cl.$^6$ .................................................. A61F 13/00
[52] U.S. Cl. ........................................... 424/449; 424/448
[58] Field of Search ................................... 424/448, 449

[56] References Cited

U.S. PATENT DOCUMENTS

| | | | |
|---|---|---|---|
| 4,412,036 | 10/1983 | Pedersen | 525/54.26 |
| 4,452,808 | 6/1984 | Gallagher, Jr. | 514/418 |
| 4,731,391 | 3/1988 | Garvey | 521/137 |
| 4,906,463 | 3/1990 | Cleary et al. | 424/449 |
| 4,912,126 | 3/1990 | Owen | 514/418 |
| 4,915,950 | 4/1990 | Miranda et al. | 424/448 |
| 4,985,467 | 1/1991 | Kelly | 521/52 |
| 5,091,186 | 2/1992 | Miranda et al. | 424/448 |
| 5,118,779 | 6/1992 | Szycher | 528/75 |
| 5,120,546 | 6/1992 | Hansen | 424/449 |
| 5,124,157 | 6/1992 | Colley et al. | 424/448 |
| 5,160,328 | 11/1992 | Cartmell | 604/307 |
| 5,203,768 | 4/1993 | Haak | 604/20 |
| 5,216,098 | 6/1993 | Ahmed | 526/288 |
| 5,246,705 | 9/1993 | Venkatraman et al. | 424/448 |
| 5,464,628 | 11/1995 | Jalonen | 424/448 |
| 5,503,843 | 4/1996 | Santus | 424/448 |

FOREIGN PATENT DOCUMENTS

| | | |
|---|---|---|
| 94/07468 | 4/1994 | WIPO . |
| 97/09971 | 3/1997 | WIPO . |
| 97/24148 | 7/1997 | WIPO . |

OTHER PUBLICATIONS

R.J. Eden et al., "Preclinical Pharmacology of Ropinirole (SK&F 101468–A) a Novel Dopamine $D_2$ Agonist", *Pharmacol. Biochem. & Behavior* 38:147–154 (1991).

*Primary Examiner*—D. Gabrielle Brouillette
*Attorney, Agent, or Firm*—Dianne E. Reed; Bozicevic & Reed

[57] ABSTRACT

Transdermal administration of certain indolone derivatives which are dopamine $D_2$ agonists is described. The method involves treating an individual afflicted with Parkinson's disease by administering an indolone derivative, e.g., ropinirole base or a pharmaceutically acceptable ropinirole salt, through the skin or mucosal tissue, for a time period and at an administration rate effective to alleviate the symptoms of the disease. Pharmaceutical formulations and drug delivery systems for administering the drugs are provided as well.

42 Claims, 4 Drawing Sheets

TRANSDERMAL ADMINISTRATION OF ROPINIROLE AND ANALOGS THEREOF

CROSS-REFERENCE TO RELATED APPLICATION

This application is a continuation-in-part of U.S. patent application Ser. No. 08/537,325, filed Sep. 29, 1995, now abandoned.

TECHNICAL FIELD

This invention relates generally to transdermal drug delivery, and more particularly relates to methods and drug delivery systems for administering ropinirole and other indolone derivatives transdermally. The invention additionally relates to pharmaceutical compositions formulated for transdermal administration of such compounds.

BACKGROUND

The delivery of drugs through the skin provides many advantages; primarily, such a means of delivery is a comfortable, convenient and noninvasive way of administering drugs. The variable rates of absorption and metabolism encountered in oral treatment are avoided, and other inherent inconveniences—e.g., gastro-intestinal irritation and the like—are eliminated as well. Transdermal drug delivery also makes possible a high degree of control over blood concentrations of any particular drug.

Skin is a structurally complex, relatively thick membrane. Molecules moving from the environment into and through intact skin must first penetrate the stratum corneum. They must then penetrate the viable epidermis, the papillary dermis, and the capillary walls into the blood stream or lymph channels. To be so absorbed, molecules must overcome a different resistance to penetration in each type of tissue. Transport across the skin membrane is thus a complex phenomenon. However, it is the cells of the stratum corneum which present the primary barrier to absorption of topical compositions or transdermally administered drugs. The stratum corneum is a thin layer of dense, highly keratinized cells approximately 10–15 microns thick over most of the body. It is believed to be the high degree of keratinization within these cells as well as their dense packing which creates in most cases a substantially impermeable barrier to drug penetration.

Relatively recent advances in transdermal drug delivery have enabled effective administration of a variety of drugs through the skin. These advances include the development of a number of skin penetration enhancing agents, or "permeation enhancers," to increase skin permeability, as well as non-chemical modes for facilitating transdermal delivery, e.g., the use of iontophoresis, electroporation or ultrasound. Nevertheless, the number of drugs that can be safely and effectively administered through the skin, without concomitant problems such as irritation or sensitization, remains limited.

The present invention is directed to the transdermal administration of certain indolone derivatives and their salts. These indolone derivatives are described in U.S. Pat. No. 4,452,808 to Gallagher, Jr., issued Jun. 5, 1984, and in U.S. Pat. No. 4,912,126 to Owen, issued Mar. 27, 1990, both of which are assigned to SmithKline & French Laboratories Limited. Reference may be had thereto for any information concerning the indolone derivatives used in conjunction with the present invention and not explicitly included herein.

A particular compound of interest is ropinirole, 4-[2-(dipropylamino)ethyl]-1,3-dihydro-2H-indol-2-one, and analogs and pharmaceutically acceptable salts thereof.

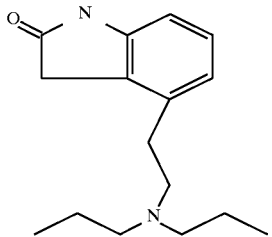

Ropinirole

Ropinirole is a novel dopamine $D_2$ agonist used in the treatment of Parkinson's disease; the compound has a molecular weight of 296.84 and a melting point of approximately 247° C. Ropinirole hydrochloride has a solubility of 133 mg/ml in water at 20° C.

Earlier methods for treating Parkinsonism typically involved the use of L-Dopa; see, e.g., S. Fahn, "'On-Off' Phenomenon with L-Dopa Therapy in Parkinsonism: Clinical and Pharmacological Correlations and the Effect of Intramuscular Pyridoxine," *Neurology* 24:431–441 (1974) and C. D. Marsden et al., "'On-Off' Effects in Patients with Parkinson's Disease on Chronic Levadopa Therapy," *Lancet* I:262–296 (1976). However, as explained in these articles, patients undergoing treatment with L-Dopa have frequently experienced severe therapeutic response fluctuations, possibly resulting from decreased capacity to store newly synthesized dopamine within the brain as a consequence of the progressive degeneration of dopaminergic nerve terminals. See Marsden et al., supra, and R. J. Eden et al., "Preclinical Pharmacology of Ropinirole (SK&F 101468-A) a Novel Dopamine $D_2$ Agonist," *Pharmacol. Biochem. & Behavior* 38:147–154 (1991). Also, as explained in U.S. Pat. No. 4,912,126, cited above, the combined administration of L-Dopa with a peripheral dopa-decarboxylase inhibitor such as carbidopa or benzaseride, as frequently done, can result in a number of adverse effects including nausea, vomiting, abdominal distension and psychiatric side-effects.

Ropinirole has been developed as a drug which is effective in the treatment of Parkinson's disease but which overcomes the limitations associated with L-Dopa therapy. Additionally, ropinirole has been identified as a more specific dopamine $D_2$ agonist than other dopamine agonists such as bromocriptine and pergolide.

Transdermal delivery of ropinirole and analogs thereof, as provided herein, provides a number of advantages: continuous delivery provides for sustained blood levels of the drug; the patch is easily removable if any side effects do occur; there is no first-pass effect; gastrointestinal and other side effects are substantially avoided; and the likelihood of patient acceptance is much improved. In general, steady-state, transdermal delivery of the drug seems to provide a better side effect profile overall than is typically associated with oral administration.

None of the art of which applicants are aware sets forth data on skin permeability or therapeutic administration rates with respect to ropinirole or other indolones. To the best of applicants' knowledge, then, effective transdermal administration of indolones as described herein, and ropinirole, in particular, is unknown and completely unsuggested by the art.

SUMMARY OF THE INVENTION

Accordingly, it is a primary object of the present invention to address the above-mentioned need in the art by providing methods, pharmaceutical formulations and systems for the transdermal administration of certain indolone derivatives, particularly ropinirole.

It is another object of the invention to provide a method for treating Parkinson's disease, which comprises administering an indolone derivative, as provided herein, to a patient through a predetermined area of intact skin or mucosal tissue for a time period and at an administration rate effective to alleviate the symptoms of the disease.

It is still another object of the invention to provide such a method which involves the transdermal administration of ropinirole base.

It is yet another object of the invention to provide such a method which involves the transdermal administration of a pharmaceutically acceptable ropinirole salt.

It is a further object of the invention to provide indolone-containing compositions formulated for transdermal delivery.

It is still a further object of the invention to provide a transdermal system for administering an indolone derivative as provided herein which comprises a laminated composite of a backing layer and a contact adhesive layer which contains the drug and serves as the basal surface which contacts the skin or mucosal tissue during use.

It is yet a further object of the invention to provide a transdermal system for administering an indolone derivative as provided herein which comprises a laminated composite of a backing layer, a contact adhesive layer which serves as the basal surface and contacts the skin or mucosal tissue during use, and, incorporated therebetween, a polymeric matrix which contains the drug and serves as the drug reservoir.

It is still a further object of the invention to provide a transdermal system for administering an indolone derivative as provided herein, in the form of a patch having an internal reservoir of a liquid, gel or foam with the drug dispersed or adsorbed therein.

Still further objects of the invention are to provide transdermal systems for administering an indolone derivative as provided herein, the systems containing high capacity polyurethane hydrogel drug reservoirs or reservoirs of superabsorbent material as will be described elsewhere herein.

Additional objects, advantages and novel features of the invention will be set forth in part in the description which follows, and in part will become apparent to those skilled in the art upon examination of the following, or may be learned by practice of the invention.

In one aspect of the invention, a method is provided for treating an individual afflicted with Parkinson's disease, by transdermally administering to the individual a therapeutically effective amount of an indolone compound of Formula (I) or a pharmaceutically acceptable salt thereof, for a time period and at an administration rate effective to alleviate the symptoms of the disease, e.g., tremor, dyskinesia, bradykinesia, postural instability, speech difficulties, and the like. The method is premised on the discovery that such compounds and pharmaceutically acceptable salts thereof may be administered through the skin or mucosal tissue to achieve desired systemic effects. In a preferred embodiment, a skin permeation enhancer is coadministered with the drug so as to increase permeability thereto and achieve more rapid delivery.

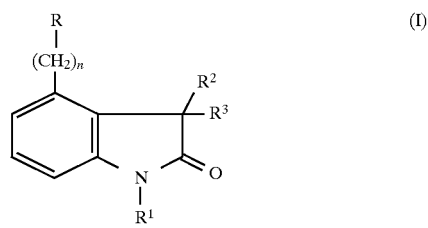

In Formula (I): R is amino, lower alkylamino, di-lower alkylamino, allylamino, diallylamino, N-lower alkyl-N-allylamino, benzylamino, dibenzylamino, phenethylamino, diphenethylamino, 4-hydroxyphenethylamino or di-(4-hydroxyphenethylamino); $R^1$, $R^2$ and $R^3$ are each hydrogen or lower alkyl; and n is 1–3.

It should be noted that while the present invention is directed to the treatment of individuals afflicted with Parkinson's disease, the present method may extend to other therapeutic uses of these indolone derivatives as well. For instance, some of the compounds encompassed by structure (I) may also have peripheral dopamine $D_2$ agonist activity and therefore may be of use in treating certain cardiovascular conditions.

In another aspect of the invention, a therapeutic system for transdermal administration of ropinirole or an analog thereof is provided. The system is a laminated composite comprising a backing layer, a drug reservoir, and a means for affixing the composite to the skin. The drug reservoir and the affixing means may be distinct, such that a separate contact adhesive layer is provided which serves as the basal surface of the device, or the drug reservoir may itself be comprised of an adhesive layer which is suitable for contacting and adhering to the skin. Such therapeutic systems are in the nature of "solid matrix" type transdermal patches. Alternative systems, containing the drug in a liquid, gel or foam reservoir, may, however, be used as well.

In still another aspect of the invention, transdermal delivery systems for administering an indolone compound of Formula (I), or a pharmaceutically acceptable salt thereof, containing high capacity urethane hydrogel drug reservoirs or reservoirs of a "superabsorbent" material as defined below. A far greater quantity of drug may be loaded into delivery devices containing such reservoirs than is possible with conventional transdermal systems. These types of systems are thus able to deliver greater quantities of drug, at higher fluxes. In addition, such transdermal delivery systems, by virtue of their high capacity drug reservoirs, also reduce or in some cases eliminate the need for skin permeation enhancers. Further, smaller transdermal patches may be made using high capacity drug reservoirs, i.e., patches that are at least as effective as prior patches in terms of overall drug release and drug flux, but are significantly reduced in terms of size.

DETAILED DESCRIPTION OF THE INVENTION

Figure 1:
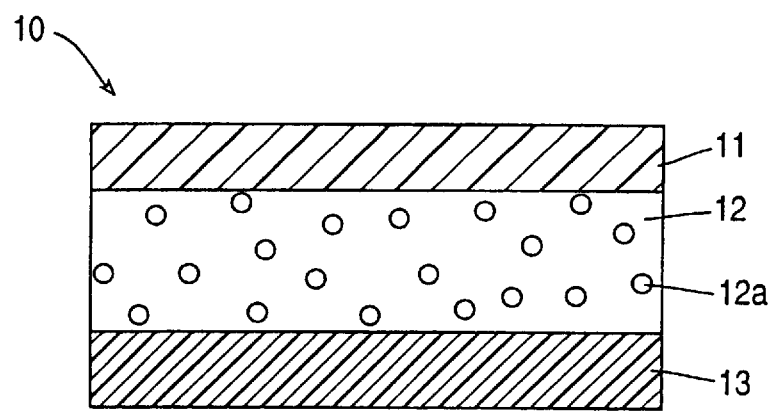
FIG. 1 illustrates in schematic form one embodiment of a solid matrix-type transdermal delivery system which may be used in conjunction with the present invention.

Before describing the present invention in detail, it is to be understood that this invention is not limited to particular formulations or transdermal systems as such may, of course, vary. It is also to be understood that the terminology used herein is for the purpose of describing particular embodiments only, and is not intended to be limiting.

It must be noted that, as used in this specification and the appended claims, the singular forms "a", "an" and "the" include plural referents unless the content clearly dictates otherwise. Thus, for example, reference to "a permeation enhancer" includes a mixture of two or more permeation enhancers, reference to "a carrier" or "a vehicle" includes mixtures of carriers or vehicles, reference to "an adhesive layer" includes reference to two or more such layers, and the like.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein.

In describing and claiming the present invention, the following terminology will be used in accordance with the definitions set out below.

By "transdermal" delivery, applicants intend to include both transdermal (or "percutaneous") and transmucosal administration, i.e., delivery by passage of a drug through the skin or mucosal tissue and into the bloodstream.

By "therapeutically effective" amount is meant a nontoxic but sufficient amount of a compound to provide the desired therapeutic effect, in the present case, that dose of ropinirole which will be effective in relieving symptoms of Parkinsonism. An "effective" amount of a permeation enhancer as used herein means an amount that will provide the desired increase in skin permeability and, correspondingly, the desired depth of penetration, rate of administration, and amount of drug delivered.

By "predetermined area of skin" is intended a defined area of intact unbroken living skin or mucosal tissue. That area will usually be in the range of about 5 cm$^2$ to about 100 cm$^2$, more usually in the range of about 10 cm$^2$ to about 100 cm$^2$, still more usually in the range of about 20 cm$^2$ to about 60 cm$^2$. However, it will be appreciated by those skilled in the art of transdermal drug delivery that the area of skin or mucosal tissue through which drug is administered may vary significantly, depending on patch configuration, dose, and the like.

The terms "indolone derivatives," "indolone analogs," "ropinirole derivatives" and "ropinirole analogs" refer to compounds having the structure of Formula (I), and pharmaceutically acceptable salts thereof. It is the transdermal delivery of these compounds which forms the basis of the present invention. In general, when transdermal administration of "ropinirole" per se is indicated herein, it is to be understood that the described method, formulation or system extends to ropinirole analogs and salts as well.

"Penetration enhancement" or "permeation enhancement" as used herein relates to an increase in the permeability of skin to a pharmacologically active agent, i.e., so as to increase the rate at which the drug permeates through the skin and enters the bloodstream. The enhanced permeation effected through the use of such enhancers can be observed by measuring the rate of diffusion of drug through animal or human skin using a diffusion cell apparatus as described in the Examples herein.

"Carriers" or "vehicles" as used herein refer to carrier materials suitable for transdermal drug administration, and include any such materials known in the art, e.g., any liquid, gel, solvent, liquid diluent, solubilizer, or the like, which is nontoxic and which does not interact with other components of the composition in a deleterious manner. Examples of suitable carriers for use herein include water, silicone, liquid sugars, waxes, petroleum jelly, and a variety of other materials. The term "carrier" or "vehicle" as used herein may also refer to stabilizers, crystallization inhibitors, or other types of additives useful for facilitating transdermal drug delivery. It will be appreciated that compounds classified as "vehicles" or "carriers" may sometimes act as permeation enhancers, and vice versa, and, accordingly, these two classes of chemical compounds or compositions may sometimes overlap.

By "high capacity" drug reservoirs, as used herein, is meant systems or reservoirs containing a amount of drug or drug formulation which is greater than that which is typically possible using conventional manufacturing techniques or transdermal drug delivery devices; the "high capacity" hydrogel drug reservoirs which may be used in conjunction with the transdermal delivery of ropinirole can be made so as to contain at least about 30 wt. % drug formulation, preferably at least about 50 wt. % drug formulation, and most preferably on the order of 70 wt. % drug formulation or more.

The term "hydrogel" is used in its conventional sense to refer to a water-swellable polymeric matrix in which a dispersed, polymeric phase has combined with a continuous, aqueous phase to form a viscous, colloidal product.

By a "superabsorbent" material, as used herein, is intended a material capable of absorbing or adsorbing an amount of fluid therein corresponding to more than 15 grams, preferably more than 25 grams, most preferably more than 50 grams, per gram of superabsorbent material. Superabsorbent materials are known that are capable of absorbing 300 to 1000 times their weight in fluids as well. Typically, superabsorbent materials are crosslinked polymers. Such superabsorbent materials not only absorb fluids but also are able to retain the fluid that has been absorbed, while remaining generally insoluble in the fluid absorbed.

The present method of transdermally delivering ropinirole or an analog thereof may vary, but necessarily involves application of a composition containing a compound of Formula (I) to a predetermined area of the skin or mucosal tissue for a period of time sufficient to provide an effective blood level of drug for a desired period of time. The method may involve direct application of the composition as an ointment, gel, cream, or the like, or may involve use of a drug delivery device as taught in the art, e.g., in commonly assigned U.S. Pat. Nos. 4,915,950, 4,906,463, 5,091,186 or 5,246,705, or as described below.

Ropinirole or an alternative indolone derivative encompassed by the structure of Formula (I) may be administered as the base or in the form of a pharmaceutically acceptable acid addition salt. As will be appreciated by those skilled in the art, the base form of the drug can be converted to an acid addition salt by treatment with a stoichiometric excess of a selected acid. Such acid addition salts may be formed, for example, with inorganic acids such as hydrochloric acid, hydrobromic acid, sulfuric acid, nitric acid, phosphoric acid, and the like, or with organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

It will generally although not necessarily be preferred to administer the compounds of Formula (I) in conjunction with a permeation enhancer, when those compounds are present in salt form. Generally, when the compounds are present in base form, an enhancer is unnecessary.

Suitable enhancers include, but are not limited to, dimethylsulfoxide (DMSO), dimethyl formamide (DMF), N,N-dimethylacetamide (DMA), decylmethylsulfoxide ($C_{10}$MSO), polyethylene glycol monolaurate (PEGML), propylene glycol (PG), propylene glycol monolaurate (PGML), glycerol monolaurate (GML), lecithin, the 1-substituted azacycloheptan-2-ones, particularly 1-n-dodecylcyclazacycloheptan-2-one (available under the trademark Azone® from Whitby Research Incorporated, Richmond, Va.), alcohols, and the like. The permeation enhancer may also be a vegetable oil as described in commonly assigned U.S. Pat. No. 5,229,130 to Sharma. Such oils include, for example, safflower oil, cotton seed oil and corn oil.

Particularly preferred enhancers for use in conjunction with the transdermal administration of indolone compounds of Formula (I) are esters given by the formula $[CH_3(CH_2)_mCOO]_nR$ in which m is an integer in the range of 8 to 16, n is 1 or 2, and R is a lower alkyl ($C_1$–$C_3$) residue that is either unsubstituted or substituted with one or two hydroxyl groups. In the preferred embodiment herein, the ester component is a lower alkyl ($C_1$–$C_3$) laurate (i.e., m is 10 and n is 1), and in a particularly preferred case is "PGML." It will be appreciated by those skilled in the art that the commercially available material sold as "PGML" is typically a mixture of propylene glycol monolaurate itself, propylene glycol dilaurate, and either propylene glycol, methyl laurate, or both. Thus, the terms "PGML" or "propylene glycol monolaurate" as used herein are intended to encompass both the pure compound as well as the mixture that is typically obtained commercially. Also preferred are analogous fatty acids, e.g., oleic acid or the like.

Other preferred enhancer compositions are wherein an ester as just described is combined with an ether component selected from the group consisting of diethylene glycol monoethyl ether and diethylene glycol monomethylether. Such enhancer compositions are described in detail in U.S. Pat. Nos. 5,053,227 and 5,059,426 to Chiang et al., both of common assignment herewith.

Still other preferred enhancer composition are wherein an ester as just described, particularly PGML, is combined with benzyl alcohol and a $C_2$–$C_6$ alkanediol. Such enhancer compositions are described in detail in PCT Publication No. WO95/05137, published Feb. 23, 1995.

The amount of enhancer present in the composition will similarly depend on a number of factors, e.g., the strength of the particular enhancer, the desired increase in skin permeability, rate of administration, and amount of drug delivered.

Preferred compositions, unless incorporated into a drug delivery system as described below, will typically contain on the order of about 0.01 wt. % to 10 wt. % drug, and about 1.0 wt. % to 20.0 wt. % enhancer, with the remainder of the composition comprising a carrier as defined above. The enhancer portion of the composition may contain a single enhancer or it may be a mixture of enhancers.

One type of transdermal system for transdermally administering an indolone compound of Formula (I) is shown in FIG. 1. The composite, generally designated 10, comprises a backing layer 11, a reservoir layer 12 containing drug 12a either dispersed therein, or adsorbed or absorbed by a particulate hydrophilic material, and a release liner 13.

The backing layer 11 functions as the primary structural element of the device and provides the device with much of its flexibility, drape and, preferably, occlusivity. The material used for the backing layer should be inert and incapable of absorbing drug, enhancer or other components of the pharmaceutical composition contained within the device. The backing is preferably made of one or more sheets or films of a flexible elastomeric material that serves as a protective covering to prevent loss of drug and/or vehicle via transmission through the upper surface of the device, and will preferably impart a degree of occlusivity to the device, such that the area of the skin covered on application becomes hydrated. The material used for the backing layer should permit the device to follow the contours of the skin and be worn comfortably on areas of skin such as at joints or other points of flexure, that are normally subjected to mechanical strain with little or no likelihood of the device disengaging from the skin due to differences in the flexibility or resiliency of the skin and the device. Examples of materials useful for the backing layer are polyesters, polyethylene, polypropylene, polyurethanes and polyether amides. The layer is preferably in the range of about 15 microns to about 250 microns in thickness, and may, if desired, be pigmented, metallized, or provided with a matte finish suitable for writing.

The reservoir layer 12 in FIG. 1 doubles as the means for containing drug and as an adhesive for securing the device to the skin during use. That is, as release liner 13 is removed prior to application of the device to the skin, reservoir layer 12 serves as the basal surface of the device which adheres to the skin. Reservoir layer 12 is comprised of a pressure-sensitive adhesive suitable for long-term skin contact. It must also be physically and chemically compatible with the indolone analog and the carriers and vehicles employed. The reservoir layer will generally range in thickness from about 10 to about 100 microns, preferably approximating 75 microns. Suitable materials for this layer include, for example, polysiloxanes, polyisobutylenes, polyacrylates, polyurethanes, plasticized ethylene-vinyl acetate copolymers, low molecular weight polyether amide block polymers (e.g., PEBAX), tacky rubbers such as polyisobutene, polystyrene-isoprene copolymers, polystyrene-butadiene copolymers, and mixtures thereof. Presently preferred adhesive materials for use as reservoir layer 12 are acrylates, silicones and polyurethanes.

Release liner 13 is a disposable element which serves only to protect the device prior to application. Typically, the release liner is formed from a material impermeable to the drug, vehicle and adhesive, and which is easily stripped from the contact adhesive. Release liners are typically treated with silicone or fluorocarbons. Silicone-coated polyester is presently preferred.

In a variation on this embodiment, reservoir layer 12 comprises a matrix of a continuous hydrophobic polymer phase, with a particulate phase of a hydrated inorganic silicate and drug adsorbed or absorbed thereby. Such a system is described, for example, in co-pending, commonly assigned U.S. patent application Ser. No. 08/056,076, filed Apr. 30, 1993, and entitled "Two-Phase Matrix for Sustained Release Drug Delivery Device" (published internationally as WO94/07468 on Apr. 14, 1994). As explained in that application, polymers which may be used as the continuous hydrophobic phase are polysiloxanes, polyisobutylene, solvent-based hydrophobic polyacrylates, polyurethanes, plasticized ethylene-vinyl acetate copolymers, low molecular weight polyether block amide copolymers, styrene-butadiene polymers, and vinyl acetate-based adhesives, with the hydrophobic polymer normally constituting about 30 wt. % to 95 wt. %, more typically 40 wt. % to 60 wt. %, of the matrix. The dispersed inorganic silicate is in the form of particulates that are typically in the non-colloidal size range of 0.001 to 0.1 mm, more usually 0.01 to 0.05 mm.

Preferably, the matrix in this embodiment additionally contains a dispersing agent which aids in maintaining the particulate phase dispersed in the continuous phase. Anionic, cationic, amphoteric or nonionic dispersing agents may be used. Preferably, the dispersing agent is a non-ionic surfactant such as a polyethylene-polyoxypropylene glycol copolymer (e.g., that sold under the "Pluronic" trademark) or a polyoxyethylene sorbitan ester (e.g., that sold under the "Tween" trademark); the dispersing agent will normally constitute about 0.5 wt. % to 10 wt. % of the matrix, more usually 3 wt. % to 6 wt. % of the matrix.

These matrices are prepared by dissolving the drug in water (with, optionally, additional hydrophilic polar solvents) and contacting the hydrophilic particulate material with the resulting solution to permit the aqueous solution to be absorbed by the particulate material. The mixture will typically have the texture of a paste. The hydrophobic components of the matrix and the dispersing agent, preferably in admixture, are added to the paste with vigorous mixing to form a viscous dispersion. This dispersion may be formed into appropriate shapes and excess solvent removed therefrom.

Figure 2:
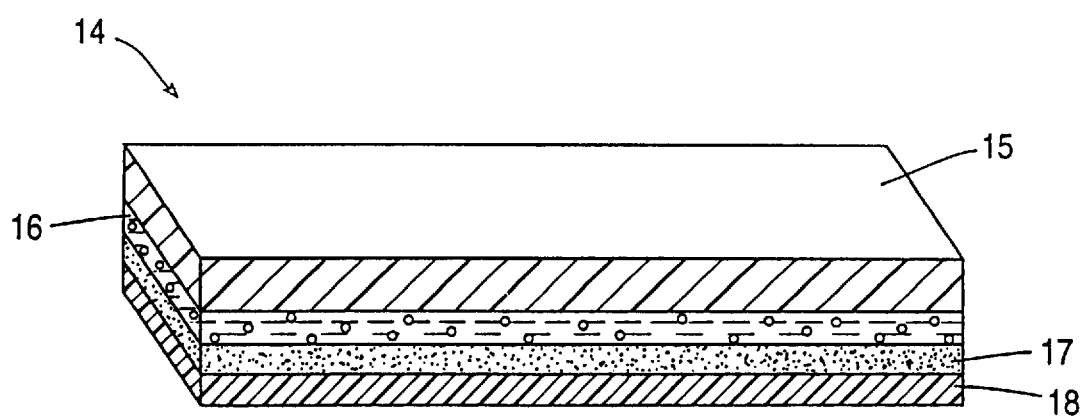
FIG. 2 illustrates in schematic form an alternative embodiment of a solid matrix-type transdermal delivery system which may be used in conjunction with the present invention.

FIG. 2 illustrates a different type of laminated composite that may serve as the transdermal delivery system herein. That system is shown generally at 14, with backing layer 15, drug reservoir 16, contact adhesive layer 17, and release liner 18. The backing layer and release liner are as described above with respect to the structure of FIG. 1. With regard to drug reservoir 16 and contact adhesive layer 17, suitable materials are as described above, e.g., polysiloxanes, polyisobutylenes, polyacrylates, polyurethanes, plasticized ethylene-vinyl acetate copolymers, low molecular weight polyether amide block polymers, tacky rubbers, and mixtures thereof.

Figure 3:
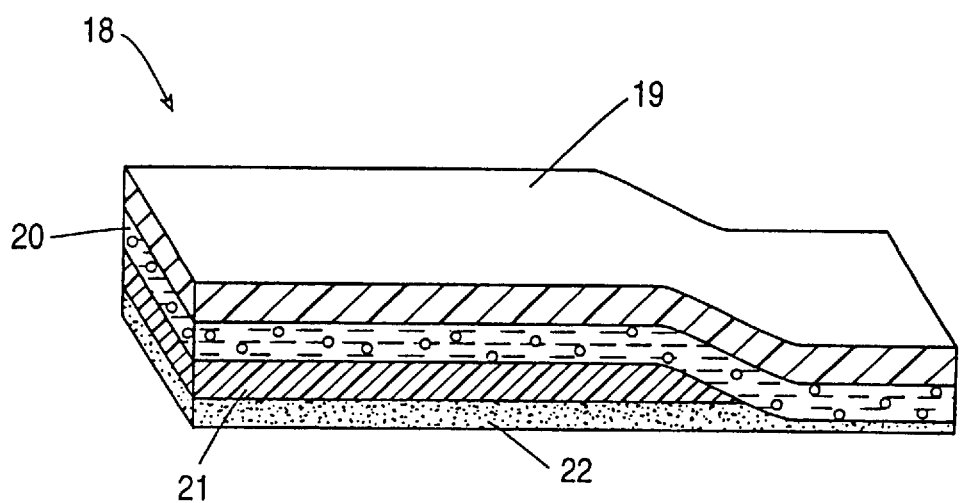
FIG. 3 illustrates in schematic form a liquid reservoir-type transdermal delivery system which may be used in conjunction with the present invention.

FIG. 3 depicts an alternative device structure for administering ropinirole or an analog thereof transdermally. The device is a "liquid reservoir" type and is generally designated 18. It comprises a top, impermeable backing layer 19, an underlying liquid, gel or foam layer 20, generally a liquid layer, containing the drug and any associated materials, e.g., enhancers or the like, that is sealed at its edge to the overlying backing layer to form a pouch between the backing and the underlying modulator layer 21, and a pressure-sensitive adhesive layer 22 that serves as the basal surface of the device and affixes the device to the skin during use. The modulator layer is generally a thin, flexible layer of a highly porous material such as polyester, polyethylene, polypropylene, or the like. As with the above embodiments, the device of FIG. 3 is provided with a release liner (not shown) to protect adhesive layer 22 prior to use. Such devices are described, for example, in commonly assigned U.S. Pat. No. 5,124,157 to Colley et al.

Figure 5:
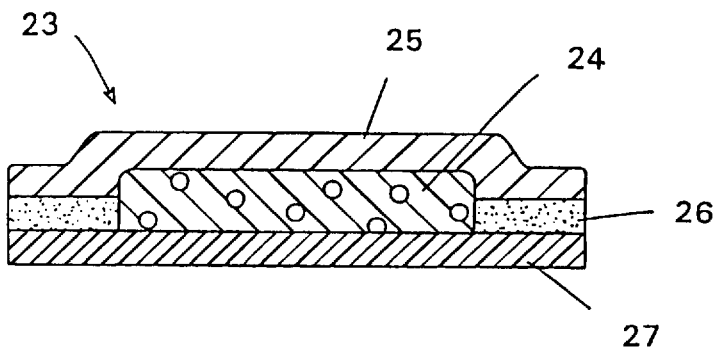
FIG. 5 is a sketch in sectional view through a transdermal delivery system for administering ropinirole, containing a drug reservoir of a superabsorbent matrix and having a peripheral adhesive.

FIG. 5 illustrates generally at 23 an additional embodiment of a laminated ropinirole delivery system according to the invention. The device 23 contains a reservoir in the form of polymeric matrix 24 containing drug, vehicle, enhancer, and the like. The backing layer, comprised of the same materials and serving the same purpose as described above with respect to FIGS. 1 through 3, is present at 25; the release liner, similarly, is present at the underside of the device at 27. A peripheral adhesive ring 26 serves to secure the device to the skin during use, and is comprised of a pressure-sensitive skin contact adhesive such as those described above for layer 12 in the device of FIG. 1. Preferred adhesive materials are acrylates, silicones and polyurethanes.

Figure 6:
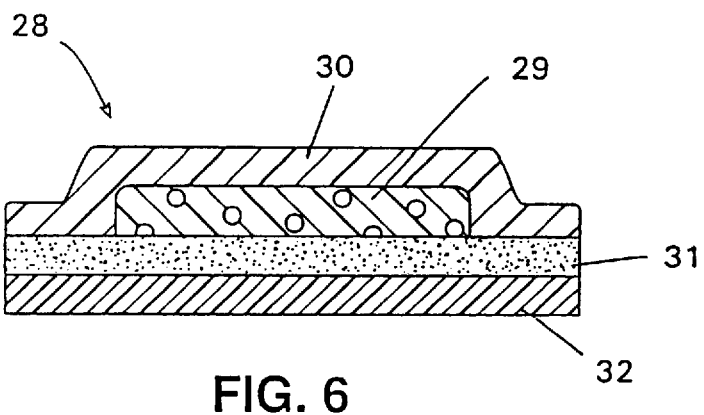
FIG. 6 is a sketch in sectional view through a transdermal delivery system for administering ropinirole, containing a drug reservoir of a superabsorbent matrix and having an in-line adhesive.

FIG. 6 depicts still an additional embodiment of the invention, shown generally at 28. Polymer reservoir 29, backing layer 30 and release liner 32 are as described with respect to FIG. 5; however, the adhesive in this embodiment is an in-line adhesive layer shown at 31. Suitable adhesive materials are pressure-sensitive skin contact adhesives as described earlier.

Figure 7:
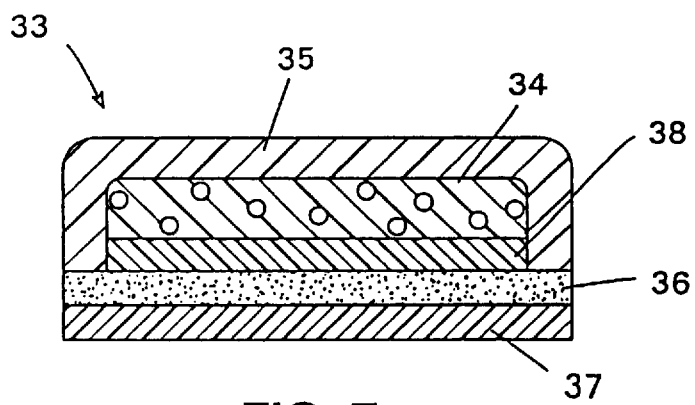
FIG. 7 is a sketch in sectional view through a transdermal delivery system for administering ropinirole, containing a drug reservoir of a superabsorbent matrix and having an in-line adhesive and an in-line membrane.

FIG. 7 illustrates still a further embodiment of the invention, shown generally at 33. Drug reservoir 34, backing layer 35, in-line adhesive layer 36 and release liner 37 are as described with respect to FIG. 6; however, in this embodiment, an in-line rate-limiting membrane is present at 38, laminated between the drug reservoir and the skin contact adhesive. Generally, as will be explained below, such a membrane is formed from materials selected to limit the flux of non-drug components from the drug reservoir, while not limiting the flux of the drug.

Transdermal drug delivery systems for use in conjunction with the administration of indolone derivatives of Formula (I) can be fabricated using conventional coating and laminating techniques and equipment which are known to those skilled in the art, and/or explained in the literature. In general, devices of the invention are fabricated by solvent evaporation film casting, thin film lamination, die cutting, or the like.

Particularly preferred transdermal systems for administering indolone compounds of Formula (I) or pharmaceutically acceptable salts thereof are those containing high capacity polyurethane hydrogel drug reservoirs, as described in commonly assigned U.S. patent application Ser. No. 08/581,128, entitled "TRANSDERMAL DRUG DELIVERY SYSTEMS HAVING POLYURETHANE HYDROGEL DRUG RESERVOIRS, AND ASSOCIATED METHODS OF MANUFACTURE AND USE," as well as those containing drug reservoirs fabricated from "superabsorbent" materials, such as described in commonly assigned U.S. patent application Ser. No. 08/528,655, entitled "TRANSDERMAL DRUG DELIVERY SYSTEMS HAVING SUPERABSORBENT DRUG RESERVOIRS, AND ASSO- CIATED METHODS OF MANUFACTURE AND USE," both of which were filed on Dec. 29, 1995.

Hydrogel-based systems:

As explained in U.S. Ser. No. 08/581,128, drug reservoirs of hydrogel-based transdermal systems will typically comprise polyurethane hydrogel matrices. These matrices may be formed by admixing a polyurethane with a suitable crosslinking agent, in the presence of water. Drug formulation may be incorporated into the hydrogel during hydrogel manufacture, i.e., admixed with the polyurethane along with the crosslinking agent and water, or it may be incorporated into the hydrogel after manufacture, i.e., after water is added.

Suitable polyurethanes useful for forming the hydrogel reservoir may be chemically synthesized using conventional techniques known to those skilled in the art or described in the pertinent literature. The polyurethanes can be polyurethane elastomers such as those available as Airthane®, Polathane®, Ultracast® and Cyanaprene® from Air Products and Chemicals Inc., as Conathane® from Conap, Inc., as Bayte C®, Baymidur Vul Kollan®, Baydur®, Bayflex® or Baygal® from Miles Inc., Polymers, Division; alternatively, polyurethane resins such as Desmodur® or Mondur® resins, which can be obtained from Miles, Inc., Industrial Chemicals Division, can be used. Hydrophilic polyurethane prepolymers such as those available under the Hypol® trademark from W. R. Grace & Co., Organic Chemicals Division, may be used as well, and are particularly preferred; and an example of a particularly effective commercially available polyurethane that can be used in conjunction with the present invention is Hypol® PreMA G-50 polymer, available from the Hampshire Chemical Corporation.

In order to form the hydrogel, a crosslinking agent is added to the polyurethane in the presence of water. Preferred crosslinking agents are diisocyanates, including aliphatic, cycloaliphatic and aromatic diisocyanates. Suitable diisocyanates include, but are not limited to, tetramethylene diisocyanate, hexamethylene diisocyanate, trimethylene diisocyanate, trimethylhexamethylene diisocyanate, cyclohexyl-1,2-diisocyanate, cyclohexylene-1,4-diisocyanate, 2,4-toluene diisocyanate, and 2,6-toluene diisocyanate. The amount of crosslinking agent used will be such that it is effective to produce the desired hydrogel, but preferably less than that which would result in any unconsumed material. However, if excess crosslinking agent is present after hydrogel formation, it may be removed using a simple washing step.

Generally, the reaction mixture for forming the polyurethane hydrogel will contain about 5 wt. % to 25 wt. % isocyanate crosslinking agent and about 0.01 wt. % to 15 wt. % water, with the polyurethane representing the remainder of the composition, along with the drug formulation, if it is incorporated during manufacture. It will be appreciated by those skilled in the art, however, that the various components of the reservoir may need to be varied, e.g., depending on the degree of tack desired (which would in turn necessitating a higher fraction of water) or on some other desired characteristic of the final product.

The drug formulation may be incorporated into the hydrogel during hydrogel formation or subsequent thereto. Generally, the latter procedure is preferred, as a greater degree of drug may be incorporated into the hydrogel; that is, by absorbing drug into the hydrogel after the hydrogel is prepared, drug loading of as high as 65 wt. % to 70 wt. % or higher can be achieved.

In an alternative embodiment, a photocurable polyurethane is used at the outset, to form the hydrogel. In such a case, curing may be effected using radiation of a suitable wavelength, rather than a crosslinking agent. Photocuring can in some cases be neater, and done more rapidly, than curing using a diisocyanate-type crosslinking agent. With photocuring, it is typically necessary to carry out the curing step in the presence of a photoinitiator. Suitable photoinitiators are radical photoinitiators that are well known to those skilled in the art. Examples of such photoinitiators include $\alpha$-alkoxy deoxybenzoins, $\alpha,\alpha$-dialkoxy deoxybenzoins, $\alpha,\alpha$-dialkoxy acetophenones, 2-hydroxy-2,2-dialkyl acetophenones, benzophenones, thioxanthones, benzils, and other compounds identified by H. J. Hageman et al., "Photoinitiators and Photocatalysts for Various Polymerisation and Crosslinking Processes," in *Radiation Curing of Polymers II*, ed. D. R. Randell (The Royal Society of Chemistry, 1991), at pp. 46–53.

The reservoir layer will generally although not necessarily range in thickness from about 1 to about 100 mils, preferably in the range of approximately 25 to 60 mils. It will be appreciated that the thickness of the reservoir will depend, however, on a variety of considerations, including the quantity of drug to be incorporated in the reservoir, desired patch size, and the like.

After fabrication of the hydrogel reservoir and incorporation of drug therein, the remainder of the transdermal system is manufactured. Generally, although not necessarily, a backing layer is laminated to the hydrogel reservoir following reservoir preparation. Suitable materials for the backing layer are described hereinabove with regard to the system of FIG. 1. Underneath the hydrogel reservoir, i.e., on the "skin" side thereof, may be a pharmaceutically acceptable contact adhesive for affixing the device to the skin during drug delivery. The adhesive is a pressure-sensitive adhesive suitable for long-term skin contact, as explained above with respect to the system shown in FIG. 1. Additionally, to protect the basal surface of the device during storage and just prior to use, a release liner is provided to cover the exposed hydrogel or adhesive surface. The release liner is a disposable element, as explained earlier herein.

Superabsorbent systems:

As explained in U.S. Ser. No. 08/528,655, "superabsorbent" drug reservoirs include a superabsorbent material and a drug formulation. The nature of the superabsorbent material is not critical. Typically, crosslinked polymer and/or copolymer compositions are preferred such as poly (acrylates), poly(maleic anhydrides), poly(vinyl alcohols), poly(ethylene oxides), poly(hydroxy methylenes), polysaccharides, and the like, as described in Chen et al. (1985) *Synthetic and Natural Polymers*, in Chatterjee (Ed.) *Absorbency*, chapter VI, pp. 197–216 (Elsevier, Amsterdam). Specific examples of superabsorbent materials include but are not limited to the reaction product at elevated temperature and pressure of hydrolyzed starch polyacrylonitrile graft copolymer, optionally having added thereto a polyhydric alcohol such as glycerol (see, U.S. Pat. Nos. 4,467,012 and 4,412,036 to Pedersen et al.), a polymer network of a crosslinked polyurethane that is prepared from an isocyanate-terminated poly(oxyalkylene)polyol and a substantially linear addition polymer containing functional groups selected from the group consisting of carbamoyl, substituted carbamoyl and carboxy, and the alkali metal and ammonium salts thereof, the chemical structure and preparation of which is described in U.S. Pat. No. 4,731,391 to Garvey, a skeletal network of a cellular polymer, preferably polyurethane, foam containing a superabsorbent material such as carboxymethyl cellulose, starch-grafted sodium polyacrylate and sodium polyacrylate as disclosed in U.S. Pat. No. 4,985,467 to Kelly et al., or a superabsorbent crosslinked ampholytic ion pair copolymer, for example, the ammonium cation 3-methacrylamidopropyltrimethylammonium and a sulfonate anion such as sulfonate, 2-methylacryloyloxyethane sulfonate, vinyl sulfonate, styrene sulfonate, or the like, as disclosed in U.S. Pat. No. 5,216,098 to Ahmed et al. Other such superabsorbent materials are well known to those of ordinary skill in the art. Preferably, the superabsorbent material an olefin/alkyl carboxylate copolymer, more preferably the superabsorbent material is a maleic anhydride-isobutylene copolymer (as may be obtained as Fiberdri® superabsorbent fibers from Camelot Superabsorbents Incorporated, Charlotte, N.C.). A superabsorbent film comprising such a copolymer may be obtained from Concert Industries Limited (Thurso, Quebec, Canada).

Skin permeation enhancers may also be present in the superabsorbent reservoir; if enhancers are incorporated, they will generally represent on the order of approximately 1 wt. % to 25 wt. % of the drug formulation. Suitable enhancers include, but are not limited to, those enhancers set out hereinabove, e.g., DMF, DMA, DMSO and the like.

Preferred drug formulations, i.e., the drug-containing composition which is loaded into the drug reservoir, will typically contain on the order of about 0.1 wt. % to 20 wt. %, preferably about 1 wt. % to 10 wt. % drug, with the remainder of the formulation representing other components such as enhancers, vehicles or the like.

The superabsorbent reservoir is prepared by dissolving the drug in water or other suitable solvent and contacting the superabsorbent material with the resulting solution to permit the solution to be absorbed by the superabsorbent material. The solution may be applied to the superabsorbent material by any conventional method such as by dipping, coating, spraying or printing. Preferably, the drug formulation is applied by printing on the superabsorbent material using methods disclosed in U.S. Pat. No. 4,915,950 to Miranda et al. This material may then be formed into appropriate shapes used to prepare a laminated composite for incorporation into a transdermal drug delivery device.

A transdermal system containing a superabsorbent drug reservoir may be prepared as follows. An adhesive is cast onto a release liner. Solvent is evaporated therefrom, and the adhesive is then laminated onto the superabsorbent drug reservoir, which is in turn transfer-laminated onto the backing film. Alternatively, the superabsorbent drug reservoir may first be laminated to the backing layer and subsequently laminated to the precast adhesive layer. Suitable materials for these various layers are set out above with respect to the systems described earlier herein.

With respect to the embodiment of FIG. 6, when fabricated so as to contain a drug reservoir of a superabsorbent material, that device can be made by preparing the superabsorbent matrix, saturating the matrix with drug, vehicle, enhancer, and any other component to be incorporated into the reservoir, and casting the prepared matrix onto a release liner. The matrix layer is then die cut, and the marginal portions removed to provide marginal spaces among the matrix pieces on the release liner. The adhesive layer is then prepared and cast onto a sheet of the backing material, and covered with an extra sheet of liner material. The die-cut matrix and backing laminate is then laminated onto the adhesive and release liner laminate, by removing the extra release liner layer and bringing the exposed surface of the adhesive into contact with the exposed surface of the matrix and the marginal portions of the backing layer.

In any of these transdermal systems, it may be desirable to include a rate-controlling membrane between the drug reservoir and a contact adhesive layer, when one is present. The materials used to form such a membrane are selected to limit the flux of non-drug components, i.e., enhancers, vehicles, and the like, from the drug reservoir, while not limiting the flux of drug. Representative materials useful for forming rate-controlling membranes include polyolefins such as polyethylene and polypropylene, polyamides, polyesters, ethylene-ethacrylate copolymer, ethylene-vinyl acetate copolymer, ethylene-vinyl methylacetate copolymer, ethylene-vinyl ethylacetate copolymer, ethylene-vinyl propylacetate copolymer, polyisethylen polyacrylonitrile, ethylene-propylene copolymer, and the like. A particularly preferred material useful to form the rate controlling membrane is ethylene-vinyl acetate copolymer.

It is to be understood that while the invention has been described in conjunction with the preferred specific embodiments thereof, that the description above as well as the examples which follow are intended to illustrate and not limit the scope of the invention. Other aspects, advantages and modifications within the scope of the invention will be apparent to those skilled in the art to which the invention pertains.

In the following examples, efforts have been made to ensure accuracy with respect to numbers used (e.g., amounts, temperature, etc.) but some experimental error and deviation should be accounted for. Unless indicated otherwise, temperature is in degrees C. and pressure is at or near atmospheric.

All patents, patent applications, and publications mentioned herein, both supra and infra, are hereby incorporated by reference.

Experimental

Materials

Ropinirole free base and salt were provided by SmithKline Beecham. All chemicals were reagent grade.

Solubility Determination

The solubilities of ropinirole in various vehicles at room temperature were determined. Excess amounts of ropinirole were added to the vehicles and stirred overnight at room temperature. Saturated solutions of ropinirole were obtained after filtration of the excess ropinirole. Samples were diluted for HPLC assay.

Assay Methodology

Two assay methods were developed, one for analyzing skin flux samples and the other to indicate stability. For the skin flux assay, samples were analyzed by HPLC using UV-detection at 250 nm. Adequate chromatographic resolution was achieved using a Zorbax Rx-C8 column. The mobile phase was a mixture of 45% phosphate buffer (pH 3.5) and 55% acetonitrile. The retention time was about 3.0 min.

The stability indicating method used was the same as the SB method. Samples were analyzed by HPLC using UV-detection at 250 nm. A Kromasil five $\mu$m C8 column was used. The mobil phase was a mixture of 84% acetate buffer and 16% (70% acetonitrile and 30% methanol). The retention time was 18 min. with a flow rate of one ml/min flow rate.

Preparation of Prototype Systems

Simple Matrix System: Ropinirole was dispersed or dissolved in vehicles, then mixed with pressure sensitive adhesives to form a uniform adhesive mixture. This mixture was cast on a release liner with a Gardner knife. The cast film was then dried at 70° C. for 30 min. A polyester film was laminated to the casting film as a backing layer.

Two-Phase Matrix System: Ropinirole was dissolved in a buffer along with calcium silicate (Micro-Cel® E) and mixed vigorously to form a viscous hydrophilic mixture. Surfactant, vehicle, and adhesive were added to the hydrophilic mixture to form a finely dispersed mixture. This mixture was then cast onto a release film and the solvent was evaporated. A polyester film was then laminated onto the casting film.

In Vitro Skin Permeation of Ropinirole

Skin Preparation: Human cadaver skin was used for the permeation studies. The frozen skins were thawed and the epidermal layers (stratum corneum and viable epidermis) were separated from the full-thickness skin by immersing it in water at 60° C. for two min. This epidermis was either used immediately for flux studies or stored at −20° C. for later studies.

Skin permeation from vehicles: Modified Franz diffusion cells were used for evaluating the performance of vehicles for ropinirole delivery. The receiver compartment was filled with 7.5 ml of pH 7 buffer. Two hundred $\mu$l of the selected vehicles saturated with ropinirole were then placed into the donor compartment to initiate the skin flux experiments. The temperature of the diffusion cell contents was maintained at 32±1° C. At predetermined times, one ml of receiver content was withdrawn and replaced with fresh buffer. Samples were assays by HPLC.

Skin permeation from prototypes: Modified Franz cells were used for evaluating the prototype systems for delivery of ropinirole. The prototype systems were peeled off the polyester release liner and placed on top of the epidermis with the drug adhesive layer facing the stratum corneum. Gentle pressure was applied to insure full contact between the drug adhesive layer and the stratum corneum. The skin membrane with the ropinirole prototype system was then mounted carefully between the donor and the receiver compartments. The receiver compartment was filled with pH 7 buffer and the temperature was maintained at 32±1° C. throughout the experimental period. One ml of receiver content was withdrawn and replaced with fresh buffer. Samples were assayed by HPLC.

Flux determination: Skin flux ($\mu$g/cm$^2$/hr) was determined from the steady-state slope of the plot of the cumulative amount of ropinirole permeated through the skin versus time. After steady state had been established, the linear portion of the plot was used to calculate the flux from the slope. Each formulation was run in triplicate, and the values reported represent the mean and standard deviation for three cells.

Skin Irritation Studies

The skin irritation study in rabbits using a modified Draize irritation protocol. The treatments included:

1) different activities of ropinirole in the selected vehicle that gave the highest flux of ropinirole slat; and
2) ropinirole in two selected vehicles. A proprietary vehicle that has been used in skin flux studies were tested as a control.

Mineral oil was used as the negative control in the study. The mean primary irritation score for each treatment was calculated.

3) ropinirole and base in three prototype systems (36048C, 36047G and 36040F; see Table 4 in Example 3, below).

EXAMPLE 1

In Vitro Flux Studies

In vitro flux experiments with ropinirole base and ropinirole HCl were conducted as described above. Various vehicles were used. The results are set forth in Table 1.

TABLE 1

Skin Flux of Ropinirole from Selected Vehicles and Polymer Matrices

| Prototype | Formulation | Skin Flux $\mu$g/cm2/hr |
|---|---|---|
| 36040A | ropinirole base saturated in buffer pH 7 | 41.33 ± 14.8 |
| 36040B | ropinirole base in PGML | 50.03 ± 4.72 |
| 36040C | ropinirole base in PGML:PG | 47.6 ± 16.29 |
| 36040D | ropinirole base in oleic acid:PG (3:97) | 36.88 ± 25.08 |
| 36040E | 4% ropinirole base, Silicone 4202 | 15.32 ± 1.02 |
| 36040F | 4% ropinirole base, 10% PGML, Silicone 4202 | 15.30 ± 2.05 |
| 36040G | 4% ropinirole base, 10% buffer pH 7, 2% Micro-Cel ® E, 3% Tween 80, Silicone 4202 | 14.99 ± 0.87 |
| 36038A | ropinirole salt saturated in PGML | 11.10 ± 2.24 |

In Table 2, an intersubject comparison of ropinirole flux from two prototypes is presented:

TABLE 2

Intersubject Comparison of Ropinirole Flux from Two Prototypes

| Prototype | Skin Donor | Ropinirole Skin Flux ($\mu$g/cm2/hr) |
|---|---|---|
| 36048C[1] | 94–27 | 4.84 ± 0.15 |
| 36048C | 94–30 | 4.44 ± 0.30 |
| 36048C | 94–55 | 6.23 ± 0.55 |
| 36047G[2] | 94–27 | 10.47 ± 1.34 |
| 36047G | 94–30 | 13.77 ± 0.99 |
| 36047G | 94–55 | 13.02 ± 2.27 |
| 36048D[3] | 94–30 | 11.24 ± 0.55 |

[1]36048C contained 4% ropinirole salt, 15% buffer, 10% PG, 4% M-E, 3% Tween 80, Silicone 4202.
[2]36047G contained 4% ropinirole base, Silicone 4202.
[3]Solution 36038D was PGML saturated with ropinirole salt.

As may be deduced from Tables 1 and 2, formulations and systems of the invention are capable of releasing ropinirole through human skin in vitro at therapeutically effective rates.

EXAMPLE 2

Drug Delivery Using High Capacity Reservoirs (a) Ropinirole HCl was mixed to saturation in various formulations (as indicated in Table 3) and absorbed onto a highly absorbent maleic anhydride-isobutylene copolymeric film, obtained from Concert Industries Limited, Thurso, Quebec, Canada. The systems were cut into 1.25 cm$^2$ circles and applied onto skin as explained above. The prototypes are identified as numbers 1, 4 and 7 in Table 3 and the flux results are shown graphically in FIG. 4.

(b) Ropinirole HCl was mixed to saturation in various formulations and added with water to Hypol® PreMA G-50 polymer (Hampshire Chemical Corporation) (ratio of water-:polymer:vehicles was approximately 1:2:2). The mixture was cast onto a nonwoven fabric (Reemay 2250 Polyester, obtained from Tycon), dried at room temperature, and applied to skin as above. The prototypes are identified as numbers 2 and 5 in Table 3, with flux results illustrated graphically in FIG. 4.

(c) A hydrogel was formed by mixing Hypol® PreMA G-50 polymer (Hampshire Chemical Corporation) with water (ratio of water:polymer was approximately 1:2). The mixture was cast onto a nonwoven fabric (Reemay 2250 Polyester, obtained from Tycon) and dried at room temperature. The dried hydrogel was cut into discs approximately ⅝" in diameter; these discs were then soaked in various formulations (see Table 3) saturated with ropinirole HCl overnight. The prototypes are identified as numbers 3, 6 and 8 in Table 3, with flux results illustrated graphically in FIG. 4.

(d) For purposes of comparison, a simple two-phase matrix system was prepared containing ropinirole HCl in various formulations as indicated in Table 3 (prototype number 9), as was a system containing solely ropinirole HCl and Silicone 4202 (prototype 10). Flux results are illustrated graphically in FIG. 4 along with those obtained from the above systems.

Figure 4:
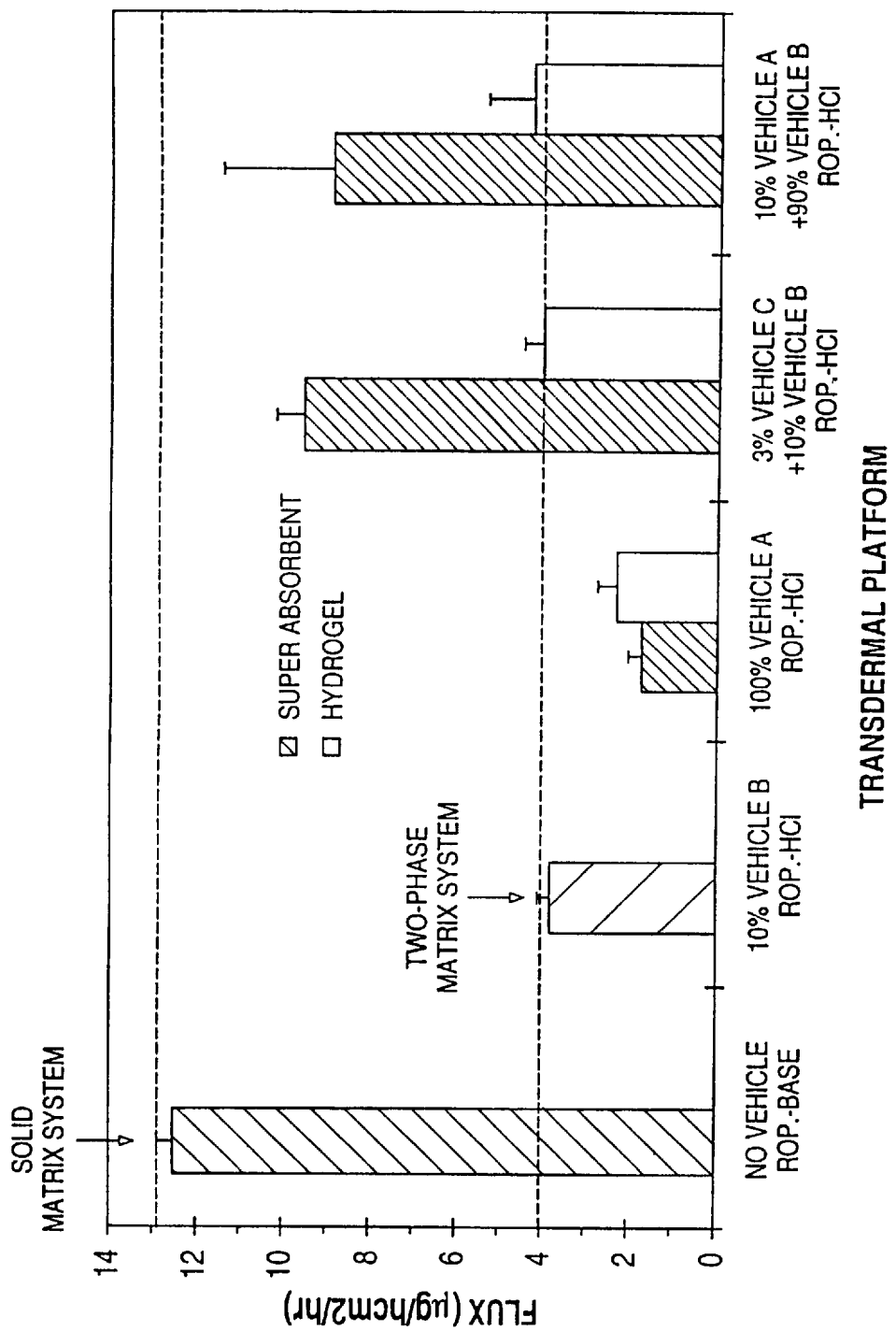
FIG. 4 is a graph illustrating the flux results obtained using various high capacity drug reservoirs for delivering ropinirole HCl (as evaluated in Example 2).

As may be deduced from the results shown in FIG. 4, transdermal systems manufactured using high capacity hydrogel reservoirs or "superabsorbent" reservoirs are quite effective in releasing ropinirole through human skin in vitro at therapeutically effective rates.

TABLE 3

Skin Flux of Ropinirole Salt from Different Prototypes

| Prototype | Formulation | Ropinirole Skin Flux ($\mu g/cm^2/hr$) |
|---|---|---|
| 1 | Superabsorbent (oleic acid:PG 3:97) | 9.74 ± 0.63 |
| 2 | Hydrogel (oleic acid:PG 3:97) | 3.96 ± 0.56 |
| 3 | Hydrogel II (oleic acid:PG 3:97) | 7.48 ± (8.71, 6.25) |
| 4 | Superabsorbent (PGML:PG 10:90) | 9.02 ± 2.51 |
| 5 | Hydrogel (PGML:PG 10:90) | 4.30 ± 1.08 |
| 6 | Hydrogel II (PGML:PG 10:90) | 22.0 ± 6.30 |
| 7 | Superabsorbent (PGML) | 1.70 ± 0.35 |
| 8 | Hydrogel II (PGML) | 2.29 ± 0.46 |
| 9 | 4% Ropinirole salt, 15% pH 7 Buffer, 4% Micro-Cel E, 10% PG, 3% Tween 80, Silicone 4202 (two-phase) | 1.91 ± 0.33 |
| 10 | 4% Ropinirole base, Silicone 4202 | 12.49 ± 0.36 |

EXAMPLE 3

Irritation Studies

Various ropinirole formulations were prepared and irritation studies conducted as described above. Results are set forth in Table 4:

TABLE 4

Primary Irritation Scores for Ropinirole Prototypes

| Prototype | Formulation | Mean Irritation Score |
|---|---|---|
| 36048C | 4% ropinirole salt, 15% pH 7 buffer, 10% PG, 4% Micro-Cel E, 3% Tween 80, Silicone 4202 | 0.7 |
| 36055A | 15% pH 7 buffer, 10% PG, 4% Micro-Cel E, 3% Tween 80, Silicone 4202 | 1.0 |
| 36047G | 4% ropinirole base, Silicone 4202 | 0 |
| 36040F | 4% ropinirole base, 10% PGML, Silicone 4202 | 2.1 |
| 36055B | 10% PGML, Silicone 4202 | 0.3 |
| 36055C | PGML | 2.5 |

It may be concluded from the results in Table 4 that the irritation encountered upon transdermal administration of ropinirole is minimal. This was a significant result, insofar as the general teaching in the art suggests that the pKa of ropinirole would be associated with a potentially significant degree of skin irritation (see B. Berner et al., "Relationship of pKa and Acute Skin Irritation in Humans," *J. Toxicol.— Cut. & Ocular Toxicol.* 8(4):481–492 (1989–1990), and B. Berner et al., "The Relationship between pKa and Skin Irritation for a Series of Basic Penetrants in Man," *Fundamental and Applied Toxicology* 15:760–766 (1990)).

EXAMPLE 4

Ropinirole Free Base Transdermal System

A solution of ropinirole free base is prepared in accordance with the following formula (all percentages are on a w/w basis of the final formulation):

| | |
|---|---|
| ropinirole free base | 4% |
| propylene glycol monolaurate | 10% |
| Dow-Corning #4202 silicone adhesive | 86% |

Ropinirole free base is obtained from SmithKline-Beecham Corporation, or may be prepared in substantial accordance with the teachings of U.S. Pat. Nos. 4,452,808 to Gallager, Jr., et al. issued Jun. 5, 1984; 4,912,126 to Owen, issued Mar. 27, 1990, the entire teachings of which are herein incorporated by reference. Dow-Corning #4202 silicone adhesive is commercially available from Dow Chemical (Midland, Mich.). Propylene glycol monolaurate is commercially available from Gattefosse (Elmsford, N.Y.).

The above components are mixed in a rotating vessel at approximately 25° C. for 1–3 hours. A substantially uniform layer of a thickness 100 microns of the above drug/adhesive mixture is applied to a 0.003" ScotchPak® #1022 polyester release liner (commercially available from 3M Corporation, St. Paul, Minn.) using a 15 mil Gardner knife apparatus by techniques well known in the art. The solvent in the is driven off by heating at 70° C. for approximately 30 minutes.

The silicone adhesive drug matrix/release liner prepared above is mated to a ScotchPak® 1012 backing layer (3M Corporation) having average cross sectional thickness of 0.002" to achieve a continuous multilayer film composition in which the saturated ropinirole drug matrix is captured between the release liner and backing layer to produce a continuous multilayer film. The continuous multilayer film is then die cut into individual units each comprising a surface area of from approximately 5–40 cm², depending on the dosage regimen to be followed and the requirements of the individual to be treated.

EXAMPLE 5

Roninirole Salt Monolithic Matrix Transdermal System

A solution of is prepared in accordance with the following formula (all percentages are on a w/w basis of the final formulation):

| | |
|---|---|
| ropinirole HCl | 4% |
| PGML | 10% |
| oleic acid | 2% |
| Dow-Corning #4202 silicone adhesive | 84% |

Ropinirole HCl is obtained from SmithKline-Beecham Corporation or may be prepared in substantial accordance with the teachings of U.S. Pat. Nos. 4,452,808 and 4,912,126.

The above components are mixed in a rotating vessel at 25° C. for 1–3 hours. A substantially uniform layer of a thickness 250 microns of the above drug/adhesive mixture is applied to a 0.003" ScotchPak® #1022 polyester release liner (commercially available from 3-M Corporation, St. Paul, Minn.) using a 15 mil Gardner knife apparatus by techniques well known in the art. The solvent in the is driven off by heating at 70° C. for approximately 30 minutes.

The silicone adhesive drug matrix/release liner prepared above is mated to a ScotchPak® 1012 polyester film backing layer (3M Corporation) having average cross sectional thickness of 0.002" to achieve a continuous multilayer film composition in which the saturated ropinirole drug matrix is captured between the release liner and backing layer to produce a continuous multilayer film. The continuous multilayer film is then die cut into individual units each comprising a surface area of from approximately 5–40 cm$^2$, depending on the dosage regimen to be followed and the requirements of the individual to be treated.

EXAMPLE 6

Ropinirole Salt Two-Phase Matrix Transdermal System

A ropinirole salt two-phase drug dispersion is prepared in accordance with the following formula (all percentages are on a w/w basis of the final formulation):

| | |
|---|---|
| ropinirole HCl | 4% |
| sodium phosphate buffer, pH 7 | 10% |
| 7% calcium silicate powder (MicroCel ® E) | 2% |
| Tween ® 80 non-ionic surfactant | 3% |
| Dow-Corning #4202 silicone adhesive | 81% |

Tween® 80 is commercially available from ICI Specialties, a division of ICI Company, Inc.

Ropinirole HCl is dissolved in buffer with the MicroCel®E and mixed vigorously to form a viscous hydrophilic mixture. The surfactant, vehicle and adhesive are added to the hydrophilic mixture to form a finely dispersed mixture. A substantially uniform layer of a thickness 100 microns of the above drug/adhesive dispersion is cast onto a 25 micron polyester film (Melinex 329, commercially available from ICI) using a 15 mil Gardner knife apparatus by techniques well known in the art. The solvent is driven off by heating at 70° C. for approximately 30 minutes.

The silicone adhesive drug matrix/release liner prepared above is mated to a 75 micron ScotchPak® 1022 polyester film backing layer (3M Corporation) to achieve a continuous multilayer film composition in which the saturated ropinirole drug matrix is captured between the release liner and backing layer to produce a continuous multilayer film. The continuous multilayer film is then die cut into individual units each comprising a surface area of from approximately 5–40 cm$^2$, depending on the dosage regimen to be followed and the requirements of the individual to be treated.

EXAMPLE 7

Ropinirole Salt Superabsorbent Transdermal System I

Dow-Corning #2675 silicone adhesive (Dow-Corning Corporation) is uniformly applied to a 0.003" ScotchPak® #1022 polyester release liner (3M Corporation) using a Gardner knife apparatus by techniques well known in the art to produce a substantially uniform layer of 2675 silicone adhesive of a thickness of approximately 0.002" on the release liner. The solvent is driven off by heating at 70° C. for approximately 30 minutes. Concert 100136 #95068 superadsorbent film (commercially available from Concert Industries Ltd., Thurso, Quebec, Canada) is uniformly applied to the silicone adhesive coated release liner.

A ScotchPak® 1012 polyester film backing layer (3M Corporation) having average cross sectional thickness of 0.002" is uniformly coated with an approximately 0.002" layer of #2675 silicone adhesive using a Gardner knife apparatus and solvent removed as described above.

A solution of vehicles is prepared containing a ratio of 3:97 oleic acid:polyethylene glycol, w/w. To this solution of vehicles, an excess of ropinirole salt (SmithKline-Beecham Corporation) is added and allowed to stand for approximately 12 hours to achieve a saturated solution of the ropinirole salt in the vehicle solution. The saturated vehicle solution is then applied to the superadsorbent layer by "printing" in substantial accordance with the teaching of Miranda, et al., U.S. Pat. No. 4,915,950, by which process the saturated solution is uniformly applied to the superadsorbent layer in the ratio of approximately 10:1 (saturated vehicle solution:superadsorbent; w/w).

The release liner/adhesive/superadsorbent layer is then mated to the silicone adhesive/backing layer to achieve a continuous multilayer film composition in which the saturated ropinirole formulation is adsorbed onto the superadsorbent matrix. The continuous multilayer film is then die cut into individual units each comprising a surface area of from approximately 5–40 cm$^2$, depending on the dosage regimen to be followed and the requirements of the individual to be treated.

EXAMPLE 8

Roninirole Salt Superabsorbent Transdermal System II

A multilayer film composition containing suberadsorbent layer containing a saturated solution of ropinirole is prepared in substantial accordance with the teachings of Example 7 above. However, an alternate solution of vehicles is incorporated into the saturated ropinirole formulation to be printed. In this instance, a solution of vehicles is prepared containing a 10:90 ratio of polyethylene glycol monolaurate:polyethylene glycol, w/w. To this solution of vehicles, an excess of ropinirole is added and allowed to stand for approximately 12 hours to achieve a saturated solution of the ropinirole in the vehicle solution. The saturated vehicle solution is then printed onto to the superadsorbent layer, mated to the silicone adhesive coated backing layer and die cut to desired dimensions in substantial accordance with the teachings of Example 7.

We claim:

1. A method for transdermally administering a therapeutically effective amount of a drug to an individual wherein the drug comprises an indolone derivative having the structure of Formula (I)

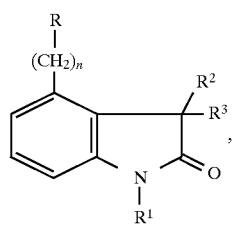

or a pharmaceutically acceptable salt thereof, by applying a transdermal drug delivery device to about 5 cm² to 100 cm² of intact skin or mucosal tissue wherein the device comprises a laminated composite of a backing layer that is substantially impermeable to the drug, and a reservoir layer having the drug dispersed therein, wherein, in Formula (I), R is amino, lower alkylamino, di-lower alkylamino, allylamino, diallylamino, N-lower alkyl-N-allylamino, benzylamino, dibenzylamino, phenethylamino, diphenethylamino, 4-hydroxyphenethylamino or di-(4-hydroxyphenethylamino), $R^1$, $R^2$ and $R^3$ are each hydrogen or lower alkyl, and n is 1–3.

2. The method of claim 1, wherein the drug is a base of the indolone derivative shown in Formula I, in which $R^1$, $R^2$, and $R^3$ are hydrogen, n is 2, and R is dipropylamino.

3. The method of claim 1, wherein the drug is a pharmaceutically acceptable salt of the indolone derivative shown in Formula I, in which $R^1$, $R^2$, and $R^3$ are hydrogen, n is 2, and R is dipropylamino.

4. The method of claim 3, wherein the pharmaceutically acceptable salt is hydrochloride salt of the indolone derivative shown in Formula I, in which $R^1$, $R^2$, and $R^3$ are hydrogen, n is 2, and R is dipropylamino.

5. The method of claim 4, wherein the skin permeation enhancer is selected from the group consisting of esters having the formula $[CH_3(CH_2)_mCOO]_nR$ in which m is an integer in the range of 8 to 16, n is 1 or 2, and R is a lower alkyl ($C_1$–$C_3$) residue that is either unsubstituted or substituted with one or two hydroxyl groups, and mixtures thereof.

6. The method of claim 5, wherein the skin permeation enhancer further comprises an ether component selected from the group consisting of diethylene glycol monoethyl ether and diethylene glycol monomethylether.

7. The method of claim 5, wherein the skin permeation enhancer further comprises benzyl alcohol and a $C_2$–$C_6$ alkanediol.

8. The method of claim 4, wherein the permeation enhancer is selected from the group consisting of propylene glycol, propylene glycol monolaurate, and combinations thereof.

9. The method of claim 1, wherein the reservoir layer is comprised of a pharmaceutically acceptable contact adhesive.

10. The method of claim 1, wherein the reservoir layer is comprised of a high capacity, polyurethane hydrogel.

11. The method of claim 1, wherein the reservoir layer is comprised of a superabsorbent, crosslinked polymeric material.

12. The method of claim 1, wherein the transdermal drug delivery device comprises a laminated composite of a backing layer that is substantially impermeable to the drug, a contact adhesive layer which defines the basal surface of the device for adhering to the skin or mucosal tissue, and, contained therebetween, a polymeric matrix containing the drug.

13. The method of claim 1, wherein the transdermal drug delivery device comprises a backing layer that is substantially impermeable to the drug, a flexible, highly porous modulator layer, a contact adhesive layer adjacent the modulator layer, which defines the basal surface of the device for adhering to the skin or mucosal tissue, with a liquid or gel reservoir between the backing layer and the modulator layer which contains the drug.

14. A system for the transdermal administration of a drug comprising an indolone derivative having the structure of Formula (I)

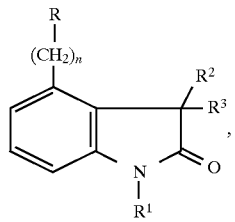

or a pharmaceutically acceptable salt thereof, comprising:
a backing layer that is substantially impermeable to the drug; and
a reservoir layer containing the drug,
wherein, in Formula (I), R is amino, lower alkylamino, di-lower alkylamino, allylamino, diallylamino, N-lower alkyl-N-allylamino, benzylamino, dibenzylamino, phenethylamino, diphenethylamino, 4-hydroxyphenethylamino or di-(4-hydroxyphenethylamino), $R^1$, $R^2$ and $R^3$ are each hydrogen or lower alkyl, and n is 1–3.

15. The system of claim 14, wherein the drug is ropinirole base.

16. The system of claim 14, wherein the drug is a pharmaceutically acceptable ropinirole salt.

17. The system of claim 16, wherein the reservoir layer additionally comprises a skin permeation enhancer in an amount to facilitate permeation of drug through the skin at a therapeutically effective rate.

18. The system of claim 17, wherein the skin permeation enhancer is selected from the group consisting of esters having the formula $[CH_3(CH_2)_mCOO]_nR$ in which m is an integer in the range of 8 to 16, n is 1 or 2, and R is a lower alkyl ($C_1$–$C_3$) residue that is either unsubstituted or substituted with one or two hydroxyl groups, and mixtures thereof.

19. The system of claim 18, wherein the skin permeation enhancer further comprises an ether component selected from the group consisting of diethylene glycol monoethyl ether and diethylene glycol monomethylether.

20. The system of claim 18, wherein the skin permeation enhancer further comprises benzyl alcohol and a $C_2$–$C_6$ alkanediol.

21. The system of claim 17, wherein the permeation enhancer is selected from the group consisting of propylene glycol, propylene glycol monolaurate, and combinations thereof.

22. The system of claim 14, wherein the drug is adsorbed or absorbed by a hydrophilic particulate material present in the reservoir.

23. The system of claim 14, wherein the reservoir layer is comprised of a pharmaceutically acceptable contact adhesive.

24. The system of claim 14, wherein the reservoir layer is comprised of a high capacity, polyurethane hydrogel.

25. The system of claim 14, wherein the reservoir layer is comprised of a superabsorbent crosslinked polymeric material.

26. A system for the transdermal administration of a drug comprising an indolone derivative of Formula (I)

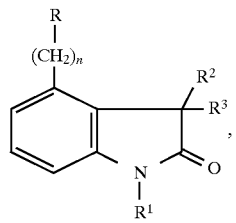

or a pharmaceutically acceptable salt thereof, comprising a laminated composite of:
  a backing layer that is substantially impermeable to the drug;
  a contact adhesive layer which defines the basal surface of the device for adhering to the skin or mucosal tissue; and, contained there between,
  a polymeric matrix containing the drug,
  wherein the system delivers the drug through an area of intact skin or mucosal tissue in the range of about 5 cm² to 100 cm², for a time period and at a therapeutically effective administration rate, and
  wherein, in Formula (I), R is amino, lower alkylamino, di-lower alkylamino, allylamino, diallylamino, N-lower alkyl-N-allylamino, benzylamino, dibenzylamino, phen-ethylamino, diphenethylamino, 4-hydroxyphenethylamino or di-(4-hydroxyphenethyl-amino), $R^1$, $R^2$ and $R^3$ are each hydrogen or lower alkyl, and n is 1–3.

27. The system of claim 26, wherein the drug is a base of the indolone derivative shown in Formula I, in which $R^1$, $R^2$, and $R^3$ are hydrogen, n is 2, and R is dipropylamino.

28. The system of claim 26, wherein the drug is a pharmaceutically acceptable salt of the indolone derivative shown in Formula I, in which $R^1$, $R^2$, and $R^3$ are hydrogen, n is 2, and R is dipropylamino.

29. The system of claim 28, wherein the polymeric matrix additionally comprises a skin permeation enhancer in an amount to facilitate permeation of drug through the skin at a therapeutically effective rate.

30. The system of claim 29, wherein the skin permeation enhancer is selected from the group consisting of esters having the formula $[CH_3(CH_2)_mCOO]_nR$ in which m is an integer in the range of 8 to 16, n is 1 or 2, and R is a lower alkyl ($C_1$–$C_3$) residue that is either unsubstituted or substituted with one or two hydroxyl groups, and mixtures thereof.

31. The system of claim 30, wherein the skin permeation enhancer further comprises an ether component selected from the group consisting of diethylene glycol monoethyl ether and diethylene glycol monomethylether.

32. The system of claim 30, wherein the skin permeation enhancer further comprises benzyl alcohol and a $C_2$–$C_6$ alkanediol.

33. The system of claim 29, wherein the permeation enhancer is selected from the group consisting of propylene glycol, propylene glycol monolaurate, and combinations thereof.

34. A system for the transdermal administration of a drug comprising an indolone derivative of Formula (I)

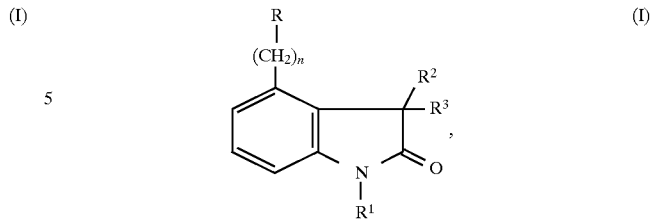

or a pharmaceutically acceptable salt thereof, comprising:
  a backing layer that is substantially impermeable to the drug;
  a modulator layer comprised of a flexible, highly porous material;
  a contact adhesive layer adjacent the modulator layer, which defines the basal surface of the device for adhering to the skin or mucosal tissue; and, between the backing layer and the modulator layer,
  a liquid, gel or foam reservoir which contains the drug,
  wherein the system delivers the drug through an area of intact skin or mucosal tissue in the range of about 5 cm² to 100 cm², for a time period and at a therapeutically effective administration rate, and
  wherein, in Formula (I), R is amino, lower alkylamino, di-lower alkylamino, allylamino, diallylamino, N-lower alkyl-N-allylamino, benzylamino, dibenzylamino, phenethylamino, diphenethylamino, 4-hydroxyphenethylamino or di-(4-hydroxyphenethyl-amino), $R^1$, $R^2$ and $R^3$ are each hydrogen or lower alkyl, and n is 1–3.

35. The system of claim 30, wherein the drug is a base of the indolone derivative shown in Formula I, in which $R^1$, $R^2$, and $R^3$ are hydrogen, n is 2, and R is dipropylamino.

36. The system of claim 30, wherein the drug is a pharmaceutically acceptable salt of the indolone derivative shown in Formula I, in which $R^1$, $R^2$, and $R^3$ are hydrogen, n is 2, and R is dipropylamino.

37. The system of claim 36, wherein the reservoir layer additionally comprises a skin permeation enhancer in an amount to facilitate permeation of drug through the skin at a therapeutically effective rate.

38. The system of claim 37 wherein the skin permeation enhancer is selected from the group consisting of esters having the formula $[CH_3(CH_2)_mCOO]_nR$ in which m is an integer in the range of 8 to 16, n is 1 or 2, and R is a lower alkyl ($C_1$–$C_3$) residue that is either unsubstituted or substituted with one or two hydroxyl groups, and mixtures thereof.

39. The system of claim 38, wherein the skin permeation enhancer further comprises an ether component selected from the group consisting of diethylene glycol monoethyl ether and diethylene glycol monomethylether.

40. The system of claim 39, wherein the skin permeation enhancer further comprises benzyl alcohol and a $C_2$–$C_6$ alkanediol.

41. The system of claim 37, wherein the permeation enhancer is selected from the group consisting of propylene glycol, propylene glycol monolaurate, and combinations thereof.

42. The method of claim 3, wherein the drug is administered along with a skin permeation enhancer.

* * * * *